United States Patent [19]
Campbell

[11] Patent Number: 4,876,901
[45] Date of Patent: Oct. 31, 1989

[54] ASBESTOS SAMPLE FILTER CLEARING SYSTEM

[75] Inventor: Jeptha E. Campbell, Cincinnati, Ohio

[73] Assignee: Spiral Systems, Inc., Cinncinnati, Ohio

[21] Appl. No.: 230,522

[22] Filed: Aug. 10, 1988

[51] Int. Cl.[4] .............................................. G01N 1/00
[52] U.S. Cl. ..................................................... 73/863
[58] Field of Search ............... 73/863, 863.11, 863.23, 73/863.25; 55/270; 422/68.08–68.14

[56] References Cited
U.S. PATENT DOCUMENTS
4,748,051  5/1988  Songer et al. ..................... 427/212

Primary Examiner—Robert R. Raevis
Attorney, Agent, or Firm—Antonelli, Terry & Wands

[57] ABSTRACT

A portable apparatus that can be used in a laboratory or at the inspection site in connection with detecting airborne asbestos which employs an acetone vapor clearing technique for cellulose ester filters exposed to airborne asbestos fibers. A metered quantity of acetone is applied to a flash vaporization chamber for each filter tested and the vapor is ducted to the filter to give an even and rapid clearing of the filter while limiting the generation of highly flammable vapors to reduce the risk of fire. This apparatus is in conformance with requirements specified in NIOSH Method 7400.

13 Claims, 2 Drawing Sheets

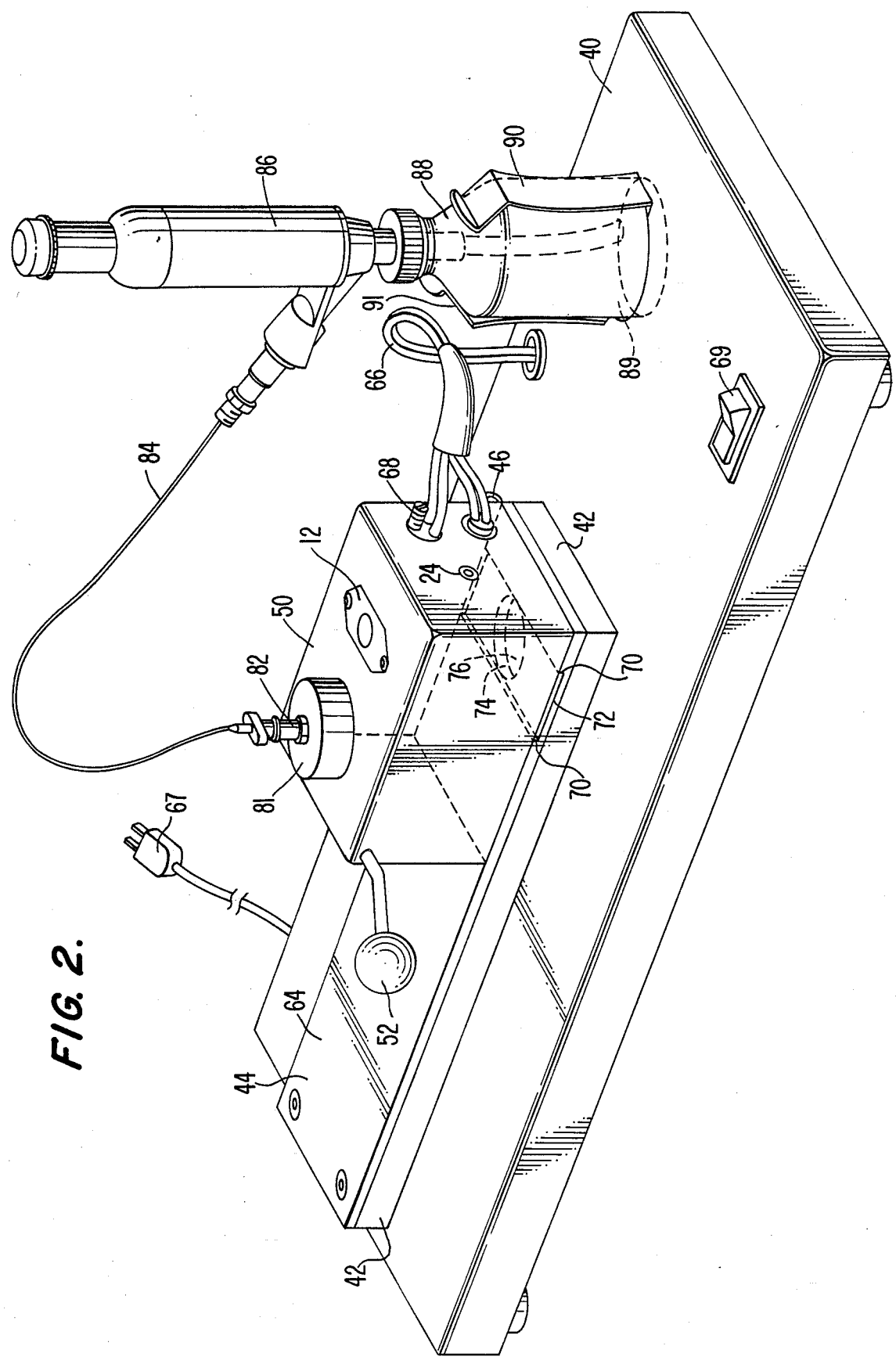

ASBESTOS SAMPLE FILTER CLEARING SYSTEM

TECHNICAL FIELD:

This invention relates to the detection of asbestos fibers and more particularly is concerned with apparatus used in a procedure for the analysis of filters that collect airborne asbestos fibers to determine concentrations of asbestos.

BACKGROUND ART:

The basic method in common use involves chemically collapsing a filter made of cellulose ester membrane onto a glass microscope slide to provide a clear background aginst which to count the individual fibers with the aid of an optical microscope. Until recently, a method recommended by National Institute of Occupational Safety and Health (NIOSH) for accomplishing the filter clearing is to use a stream of acetone vapor which is produced by heating liquid acetone to a temperature of about 56° C. The stream of acetone vapor used for clearing must be capable of rapidly collapsing the filter structure without distorting the filter or displacing the dust on the filter. Fire hazards associated with the use of acetone vapor are substantial and have restricted general use of this clearing technique without specialized equipment designed to reduce the likelihood of fire.

In the aforementioned procedure a flask of acetone is heated to cause vapor formation by continuous boiling. Ducting a vapor stream in a downward direction allows a sampling of cellulose ester filter to be positioned under the vapor stream to effect the clearing procedure. This technique makes inefficient use of acetone and poses a substantial fire hazard thus limiting its use to a ventilated fume hood.

Based on an improvement of the above method, two acetone vaporizers designed for asbestos air sample preparations have been marketed by BGI Incorporated of Waltham, MA and ETC of Monroeville, PA. These vaporizers are stated to be usable in unventilated areas and one is accompanied by an auxiliary heater that is in a separate housing. The heater has surfaces heated to about 50° C. on which a slide can be placed to complete the clearing process if necessary.

In a Revision #2 of the NIOSH Method #7400 dated Aug. 15, 1987, an aluminum "hot block" technique was recommended. This apparatus is shown in FIG. 1 of the drawings and is described in a article entitled "An Asbestos Sample Filter Clearing Procedure", by Baron, et al.

In this prior art procedure, a portion of the circular filter, usually 90° segment, has been cut and placed on a glass slide. Acetone vapors directed to the filter segment cause the cellulose ester material to clear and become essentially invisible in a period of about 5 seconds. The vapors are directed as a plume rather than as a point source so condensation occurs over the entire surface of the filter, thereby minimizing shrinkage and distortion. As in the earlier NIOSH Method #7400, one or two drops of triacetin are placed on the treated filter wedge. A glass cover slide is put over it and the edges are sealed with lacquer or nail polish to create a permanent mount.

With the FIG. 1 equipment, flash vaporization of acetone is made possible and thus the need no longer exists for continuous boiling of a quantity of acetone in a flask which was an earlier prior practice. A unitary block 10 of aluminum is heated by a suitable means such as heating pads on opposite side walls to a temperature of about 70° C. as detected by a surface thermometer 12. A blind hole 14 having a diameter of about 2.5 cm is drilled from an upper surface 16, which serves as a flash vaporization chamber, and a similar blind hole 18 is drilled from the bottom or lower surface 20 which serves as a condensation chamber 18. A horizontal connecting channel 22 is drilled from a side face 23 to interconnect the holes 14 and 18. Hole 22 is plugged as by a threaded set screw 24 to prevent vapor escape. A recess having walls 26 is machined across the bottom surface 20 to provide a notch to allow a slide 28 to be inserted over the upper surface of an unheated ceramic base 29. The filter segment is intended to be centrally located under the hole 18.

An insulating plug 30 of a synthetic resin material such as Teflon a polytetrafluoroethylene, with a small passageway 32 allows the insertion of the tip of an adjustable micropipette. Acetone liquid at ambient temperature is injected into the flash vaporization chamber 14 directly below plug 30. Acetone vapor is directed along horizontal channel 22 to hole 18 where it is directed downwardly to condense on the filter and slide surfaces. The ducting has no direct path for liquid to reach the filter. The vapor is allowed to expand and diffuse along duct 22 so that the filter is exposed to a uniform plume of acetone vapor.

In operation, the metal block 10 is placed on a smooth surface 29 usually of ceramic where the block 10 remains during the time when a number of filter segments that have been placed on separate glass slides 28 are sequentially inserted under the condensation chamber 18 where the vapor is directed downwardly. Upon removal of each slide, a drop of triacetin is applied to the center of the cleared filter and a glass coverslip is applied. Complete clearing of the filter sometimes requires an additional time which may be reduced to 15 minutes or less if placed on a surface heated to no more than about 50° C.

One problem with using the FIG. 1 device is that the filter material is very light and when placed on a glass slide 28 is influenced by electrostatic forces. Moving the slide 28 along the surface of ceramic base 29 into the slot having walls 26 under the heated block 10 is frequently accompanied by a displacement of the filter from the desired position in the center of the chamber 18. Visual observation of the final position of the filter on slide 28 is not possible.

Another problem is that over prolonged period of operation, latent heat builds up in that portion of ceramic base 29 that underlies block 10 which decreases the rate of condensation of acetone and hence the uniformity of the action of the vapor to clear the cellulose ester filter material.

SUMMARY OF INVENTION

A primary object of the present invention is to provide a novel apparatus that is safe and easy to use by personnel at any location where electric power is available. A small amount of liquid acetone may be carried safely at ambient temperature and only small amounts are released from a liquid container directly into a flash vaporization chamber without manual handling of the liquid. Acetone vapors may be ducted to the filter sections without exposure to the atmosphere, and residual vapor can be extensively diluted before allowing the vapor to escape into the atmosphere.

Another object is to provide a novel apparatus which has a heated block containing a flash vaporization chamber hingedly mounted above a metal plate so that the slide and position of the filter on the slide can be observed when the heated block is lowered into position. Undetected displacement of the filter position on the glass slide due to electrostatic charge forces can be eliminated. The metal plate may be provided with a positioning slot to assure precise alignment between the glass slide and the condensation chamber.

Yet another object of the invention is to obviate the problem of heat build-up on the slide support surface in the metal plate which detracts from the efficacy of the condensation plume. To this end, a through hole is provided in the metal plate under the slide and a volume of air is provided which allows circulation to reduce temperature build-up and collection of vapor condensate.

A further object of the invention is to provide a novel structure wherein the metal plate is mounted in an insulated manner on a support base so that the metal plate can be heated by the block and provide a surface for storing processed filters in a heated environment to hasten the completion of the clearing of the filter and shorten the period before optical examination can be started. The support base may be provided with a receptacle for carrying a container of liquid acetone and with conventional circuitry necessary for regulating the temperature of the heated block so that the entire unit is readily transportable and easy to set up and use.

These and other objects of the invention will become more fully apparent from the claims and from the description as it proceeds in conjunction with the drawings.

BRIEF DESCRIPTION OF DRAWINGS

FIG. 2 is a pictorial view of an apparatus according to the invention;

BEST MODE FOR CARRYING OUT THE INVENTION

Figure 1:
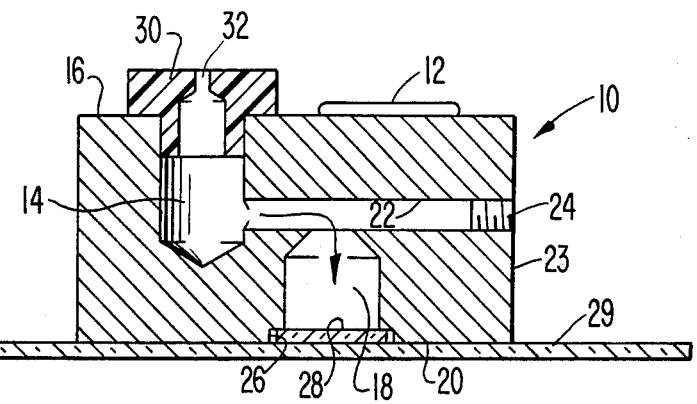
FIG. 1 is a front elevation in section of a prior art apparatus used for processing filters to have a clear background so that asbestos fiber counting can be performed with the aid of an optical microscope.

Referring now to FIG. 2, the device according to the present invention may be mounted on a base 40 of a suitable material such as metal, which is adapted to be placed on any general support surface. Mounted on the upper surface is a slab 42 of heat insulation material, such as phenolic fiberglass laminate or high density polyethylene, which supports a metal plate 44. Along the rear edge of metal plate 44 is a hinge 46 to which the block 50 of aluminum is secured. A handle with a knob 52 may be provided which is movable between the two positions illustrated in FIG. 4.

Figure 3:
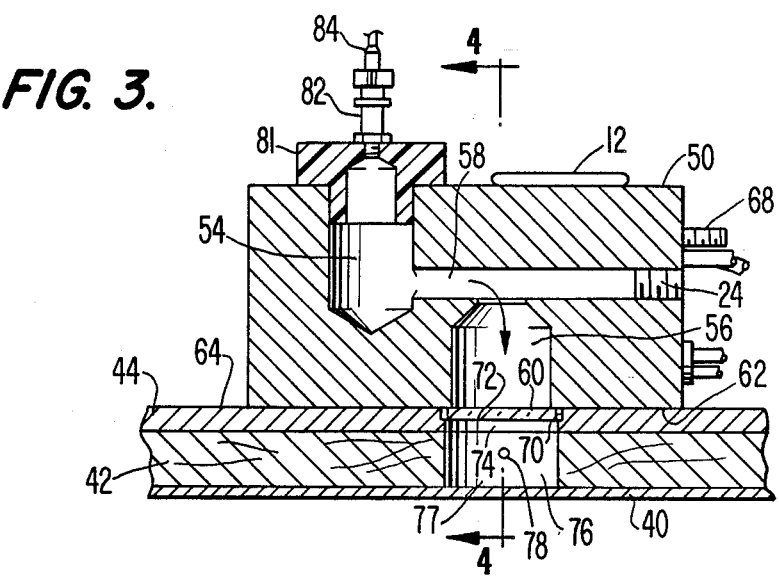
FIG. 3 is a front elevation in section similar to FIG. 1 and showing a portion of the FIG. 2 apparatus according to the present invention.
Figure 4:
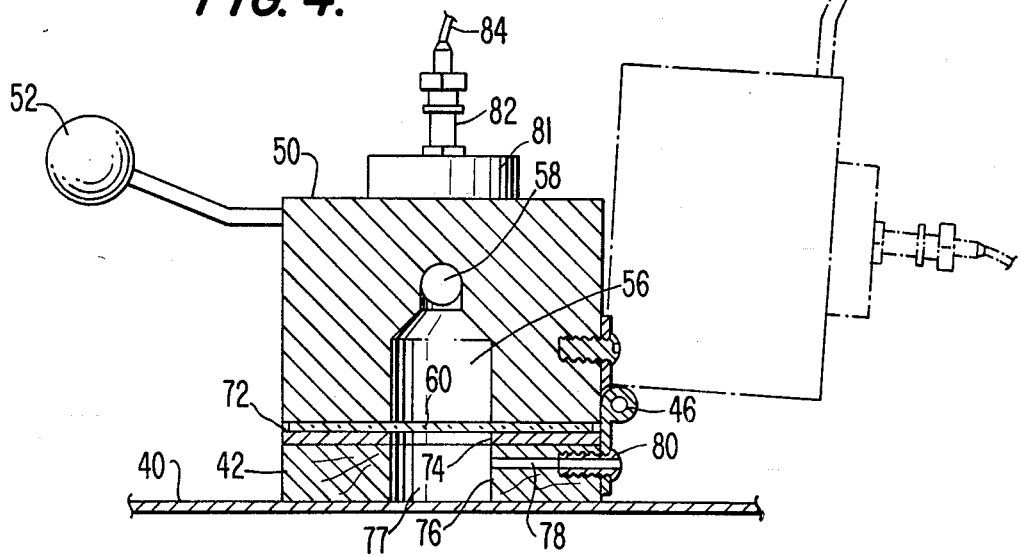
FIG. 4 is a right side elevation in section of the apparatus illustrated in FIGS. 2 and 3.

As is apparent from FIGS. 3 and 4 the block 50 has an interior flash vaporization chamber 54 and a condensation chamber 56 interconnected by duct 58 so that the vapors from chamber 54 will follow the direction of the arrow to condense on the cooler filter material carried by slide 60 as in the FIG. 1 prior art block 10. However, in accordance with one feature of this invention, block 50 may have a planar lower surface 62 which fits flush with the upper surface 64 of metal plate 44 and thus be in good heat transfer relationship. For example, when block 50 has a temperature nominally 70° C. as the result of an internal cartridge heater powered by electrical current flowing through wires 66 from plug 67 and on-off switch 69 according to a setting of a temperature control 68, the temperature of surface 64 may be about 50° C. which provides a conveniently located surface for the completion of filter clearing.

Metal plate 44 is advantageously provided with a recess having side walls 70 and a lower surface 72 to form a slot for receiving slide 60 as best shown in FIGS. 3 and 4. The lower surface 72 is provided with an aperture having a wall 74 at a central location to be under the slide 60 and in axial alignment with the condensation chamber 56. A small clearance is provided between the edges of slide 60 and the side walls 70 of the slot (see FIG. 3) to allow vapors to clear out of the chamber and to allow for the small variations in slide size. The condensation chamber 56 effectively extends through metal plate 44 and thus allows the central portion of the slide 60 where the filter is to be mounted to be free from contact with a heated underlying surface that can inhibit the condensation process.

Referring now to FIGS. 2, 3 and 4, in the heat insulating slab 42 a through hole having wall 76 in alignment with the wall 74 of the hole in plate 44 is provided which extends downwardly to the upper surface of base 40. A horizontal hole 78 is drilled from the rear surface under hinge 46 to communicate with hole 77. In the illustrated embodiment the hinge 46 is fastened, to the slab, in part by a screw 80 which is formed with a central through bore that is in alignment with horizontal hole 78 to vent acetone vapors to the rear of the unit and generally assist in keeping a cooler environment for the central portion of slide 60 which carries the filter material that is to be cleared.

Liquid acetone is injected through plug 81 which may be identical to the prior art plug 30 as described in connection with FIG. 1. An adapter 82 which is on the end of a small diameter tubing 84 of a material such as Teflon a polyentrafluoroethylene, is connected to an adjustable volume dispenser pump 86 rather than to a pipette as previously used. Tubing 84 may be connected to a pump 86 which is capable of pumping between 0.15 and 0.3 milliliters of acetone during a single stroke. Liquid acetone at ambient temperature is carried in the container 88 that is shaped to be held in a recess 89 that is in the upper surface of base 40. A pair of cantilever mounted spring arms 90, 91 may be used to secure container 88 in its desired position. Base 40 is unheated and is insulated from metal plate 44 by the slab 42 of heat insulating material.

Dispenser 86 may be adjusted to deliver exactly the desired amount, e.g. 0.2 ml, of acetone that is needed for use in the clearing process. After the slide 60 has been placed on the surface 72 in the slot between walls 70 of the metal plate, the preheated block 50 is lowered. Because of the hinge 46 and slot walls 70, the slide 60 is always at its proper position. Because the position of the filter on the slide 60 can be observed before lowering the block 50, the filter can be repeatedly positioned with ease at the center of the condensation chamber 56.

Depression of the plunger on the dispenser 86 (adjustable from 0.15 to 0.30ml) causes a metered quantity of acetone to be injected into the flash vaporization chamber 54. Within a matter of 5 seconds or less, handle 52 can be lifted and slide 60 removed to a location where triacetin is added and a coverslip applied and sealed as is the common practice.

To shorten the time required for the complete clearing of the filter, slide 60 with the coverslip may be positioned on a surface 64 of the metal plate 44 near block 50 where the heat from the block 50 maintains a metal plate temperature upwardly towards 50° C. while other filters and slides are being prepared and exposed to acetone vapors.

The rate of processing when using the present invention is variable and can be as rapid as the slides can be manipulated, or at spaced intervals with long delays between successive treatments while the apparatus remains in a standby condition without requiring significant adjustments.

Advantages of the present invention reside in the provision of a structure which allows precise positioning of the filter under the acetone vapor delivery path to facilitate uniform condensation as a consequence of a vapor path having top access over a cold filter. The slotted support surface in plate 44 provides an indexed position for the slide 60 and a liftable block facilitates insertion of the slide 60 supporting the filter by allowing visual inspection of the filter on the slide which might otherise be displaced inadvertently by physical means or static electricity. The apparatus provides a long term ability to condense because of the through apertures in the metal plate and underlying heat insulating slab and the resistance of the slab against becoming heated by an amount to diminish the condensation action. Because of the limited amount of acetone vapors that are generated and of the through apertures provided walls 74 and 76 in the metal plate 44 and slab 42, the risk of fire is negligible.

Insertion of the slide and operation of the acetone dispenser can be easily learned. The rate of handling of the sample is not critical and the adjustments necessary to use filters of different sizes can become self-evident with a little experience. An extension surface provided by the metal plate is heated sufficiently by the heat coming from the heat source which causes flash vaporization to be usable in the post treatment operation without the need for a separate piece of equipment or a separate heat source.

While only a single embodiment has been described, other variations and modifications which fall within the scope of the appended claims are intended to be covered thereby.

I claim:

1. Apparatus for clarifying asbestos fibers collected on a cellulose ester membrane filter comprising:
   a base;
   a container of liquid acetone secured to said base;
   a slide for supporting a filter;
   a metal plate having an upper surface for supporting said slide at a first position;
   means having a heat conducting relationship with said metal plate for applying acetone vapors to said filter, said means including a heated flash chamber to vaporize said acetone, said flash chamber being off-set from said first position, and heated conduit means for transporting said vapors to said first position whereby the vapors condense upon reaching said filter;
   means associated with said container for injecting a limited amount of liquid acetone to said flash chamber to restrict the quantity of vapors to the quantity needed for clearing said filter material; and
   a slab of insulating material sandwiched between said base and said metal plate whereby the metal plate is maintained at an elevated temperature relative to said base by the heat associated with said heated flash chamber.

2. Apparatus for clarifying asbestos fibers collected on a cellulose ester membrane filter comprising:
   a base;
   a container of liquid acetone secured to said base;
   a slide for supporting a portion of said filter;
   a metal plate having an upper surface for supporting said slide at a first position, said metal plate having a second position for supporting said slides, said second position being heated sufficiently by heat from said flash chamber to reduce the time required to clear the filter material on a slide supported on said second position;
   means having a heat conducting relationship with said metal plate for applying acetone vapors to said filter, said means including a heated flash chamber to vaporize said acetone, said flash chamber being off-set from said first position, and heated conduit means for transporting said vapors to said first position whereby the vapors condense upon reaching said filter;
   means associated with said container for injecting a limited amount of liquid acetone to said flash chamber to restrict the quantity of vapors to the quanity needed for clearing said filter material; and
   a slab of insulating material sandwiched between said base and said metal plate whereby the metal plate is maintained at an elevated temperature relative to said base by the heat associated with said flash chamber.

3. Apparatus for clarifying asbestos fibers collected on a cellulose ester membrane filter comprising:
   a base;
   a container of liquid acetone secured to said base;
   a slide for supporting a filter;
   a metal plate having an upper surace for supporting said slide at a first position;
   means having a heat conducting relationship with said metal plate for applying acetone vapors to said filter, said means including a heated flash chamber to vaporize said acetone, said flash chamber being off-set from said first position, and heat conduit means for transporting said vapors to said first position whereby the vapors condense upon reaching said filter;
   means assciated with said container for injecting a limited amount of liquid acetone to said flash chamber to restrict the quantity of vapors to the quantity needed for clearing said filter material;
   a slab of insulating material sandwiched between said base and said metal plate whereby the metal plate is maintained at an elevated temperature relative to said base by the heat associated with said heated flash chamber; and
   the vapor applying means comprises a block of heat conductive material mounted by a hinge means along one edge to said slab of insulating material to permit pivotal movement of said block relative to said metal plate about a horizontal pivot axis, and said apparatus further comprises a handle to lift a side of said block opposite said hinge means to facilitate loading and removal of said slide from said first position.

4. Apparatus as defined in claim 3 wherein the metal plate contains a slot in its upper surface for accurately positioning said slide when said block is raised.

5. Apparatus as defined in claim 3 wherein the base supports electrical means for controlling the rate of heat generation including an on-off switch and means for supplying operating electrical voltage to said controlling means.

6. Apparatus for detecting concentrations of fibers of a material including asbestos on a filter of a cellulose ester membrane material while supported on a slide comprising:
   means for supplying a predetermined amount of liquid acetone to a flash vaporization chamber,
   vapor conveying means for directing acetone vapors from said chamber onto said filter that is supported on an upper surface of said slide; and
   means including a plate of heat conductive material for supporting said slide at first and second positions, said first position defined by guide surfaces on an upper plate surface of said plate that is under said vapor conveying means, said second position being adjacent to said first position but remote from said vapor conveying means with heat from said flash vaporization chamber conducted to said slide supporting means to provide heat at said second position effective to accelerate the clearing process.

7. Apparatus as defined in claim 6 wherein the vapor conveying means is carried by a block of heat conductive material which contains said flash vaporization chamber, said apparatus further comprising means for mounting said block for pivotal movement about a horizontal hinge axis located at a rear side of said apparatus, and handle means attached to a front side of said block for lifting a front portion of said block to enable loading and removal of said slide at said first position.

8. Apparatus as defined in claim 7 wherein said guide surfaces are part of a slot having vertical side walls for precisely positioning the slide at said first position while said block is pivoted to its lifted position.

9. Apparatus as defined in claim 6 further including a slab of heat insulating material positioned beneath the slide support means, there being a through aperture extending vertically through said slab and said slide support means at said first position for confining excess acetone vapors, and there being a channel means effective to vent accumulated acetone vapor accumlated in said through aperture to a rear side of said apparatus.

10. Apparatus as defined in claim 9 further comprising a base underlying said slab of insulating material, said base containing an electrical cord, an on-off switch and control means for heating said flash vaporization chamber, a recess in an upper surface of said base at one side thereof, and wherein said liquid acetone supplying means includes a container for liquid acetone positioned in said recess and secured to said base, said means for supplying a predetermined amount of liquid acetone comprises an adjustable volume dispenser mounted in a sealing relationship at a top of said container, and a flexible conduit extending from said dispenser to a gas tight fitting in said flash vaporization chamber.

11. Apparatus for detecting concentrations of fibers of a material including asbestos on a filter of a cellulose ester membrane material comprising:
   a slab of heat insulating material;
   a layer of a material having good heat conducting properties supported on said slab, said layer having a horizontally extending slot on an upper surface thereof for receiving a slide adapted to carry said filter, said layer further having a vertical through aperture in said slot located at a position beneath a central portion of said slide when the slide is positioned in said slot;
   a vertical through aperture in said slab in substantial alignment with the aperture in said layer and a horizontal vent channel extending from an exterior surface of said slab through to said slab vertical aperture;
   a block of heat conductive material supported on said layer having a first chamber that opens to an upper surface of said block and a second chamber that opens to a lower surface of said block in alignment with and overlying the through apertures in said layer and slab;
   a plug sealingly mounted in the opening of said first chamber with a passageway for receiving a liquid; and
   means for heating said block to a temperature sufficiently high to vaporize in said first chamber liquid inserted through said plug passageway and to conduct said vapors into said second chamber and downwardly toward said vertical through apertures.

12. Apparatus as defined in claim 11 further including:
   a base positioned beneath said slab and closing the through aperture in said slab;
   hinge means for mounting said block for pivotal movement about one edge thereof to provide selective access to the slot in said layer of heat conducting material; and
   means for applying a limited quantity of liquid not in excess of a predetermined amount through said plug passageway when said slide is in said slot and said second chamber is positioned over said slide.

13. Apparatus as defined in claim 11, wherein the base contains a recess in an upper surface thereof together with means for securing a container for said liquid in said base, said apparatus further includes a container in said recess, a dispenser in said container and connected by a flexible fluid conduit to said plug passageway for injecting said limited quantity of liquid into said vaporization chamber on an intermittent basis.

* * * * *